United States Patent [19]

Coffey et al.

[11] Patent Number: 5,102,986
[45] Date of Patent: Apr. 7, 1992

[54] METHOD FOR CARRYING OUT ORGANIC CHEMICAL REACTIONS AND APPARTAUS FOR CARRYING OUT THAT METHOD

[75] Inventors: Andrew F. Coffey, Dunstall; Roger Epton, Kingswinford; Tony Johnson, Cambridge, all of England

[73] Assignee: Wolverhampton Polytechnic Higher Education Corporation, England

[21] Appl. No.: 659,397

[22] PCT Filed: Aug. 25, 1989

[86] PCT No.: PCT/GB89/00996
§ 371 Date: Feb. 22, 1991
§ 102(e) Date: Feb. 22, 1991

[87] PCT Pub. No.: WO90/01987
PCT Pub. Date: Mar. 8, 1990

[30] Foreign Application Priority Data

Aug. 26, 1988 [GB] United Kingdom ............... 8820256

[51] Int. Cl.⁵ ................ B01D 12/00; B01D 15/00; C07K 1/04; C07K 17/04
[52] U.S. Cl. .................... 530/334; 210/661; 210/677; 210/678; 422/193; 422/239
[58] Field of Search ............... 530/334; 422/188, 193, 422/234, 239; 210/661, 677, 678

[56] References Cited

U.S. PATENT DOCUMENTS

| | | | |
|---|---|---|---|
| 4,192,798 | 3/1980 | Verlander et al. | 530/334 |
| 4,267,056 | 5/1981 | McClure | 210/678 |
| 4,362,699 | 12/1982 | Verlander et al. | 530/334 |
| 4,801,449 | 1/1989 | Balint, Jr. et al. | 530/413 |

FOREIGN PATENT DOCUMENTS 177341 11/1982 Japan .
2161815 1/1986 United Kingdom .

Primary Examiner—Jeffrey E. Russel
Attorney, Agent, or Firm—Daniel J, Hudak Co.

[57] ABSTRACT

In carrying out an organic chemical reaction, such as the synthesis of a polypetide, it is known to attach a substance to particles of pervious support material and to immerse the particles in a sequence of liquids which serve as reagents, solvents etc. The invention provides a method in which, during at least one stage in a reaction of that kind, a liquid is introduced into a vessel containing particles of support material in such a manner that the immediately preceding liquid is progressively displaced by the incoming liquid. Apparatus for carrying out that method comprises a vessel (1) with upper and lower sintered restraining plates (5 and 6) between which the support material is located. Valves (8 and 11) can be set at will to enable a pump (13) to pump liquid into the vessel from above or below and to recirculate or discharge the liquid.

11 Claims, 2 Drawing Sheets

METHOD FOR CARRYING OUT ORGANIC CHEMICAL REACTIONS AND APPARTAUS FOR CARRYING OUT THAT METHOD

This invention relates to a method of carrying out organic chemical reactions and apparatus for carrying out that method.

The invention has largely been developed for use in carrying out the synthesis of peptides but it will be understood that it is of broader application than that and can be used in carrying out a wide range of other organic chemical reactions.

In a known type of procedure, one of the substances that takes part in a reaction is attached to particles of a pervious support material so that at least some of the substance is within the particles. The material may be relatively rigid but it is preferred to use a soft gel. In carrying out the reaction, support material to which the substance is attached has a sequence of liquids applied to it, one after another. Some of the liquids are reagents which are used to bring about steps in the reaction process, while other liquids are solvents which are used for the washing or other treatment of the support material or of the substance attached to it. Liquids serving other purposes may also be employed. It is usual to place a quantity of the support material in a vessel which is open at the top and which has an outlet at the bottom leading to a discharge tube. A tap is provided adjacent to the outlet to enable the outlet to be opened and closed at will. Downstream of the tap a branch extends laterally from the discharge tube and can be connected to a vacuum pump. Inside the vessel, above the outlet, is a transverse plate make of sintered material; liquid can pass through the pores in the plate but the pores are too small to permit the particulate support material to pass through them.

In carrying out the method a first liquid is introduced into the vessel so that the support material becomes immersed in it. The vessel is shaken to allow the liquid to come into intimate contact with the particulate support material After a predetermined period of time has elapsed the tap is opened and the first liquid is drained off through the discharge tube; a vacuum is applied to the branch and assists the withdrawal of the liquid from the vessel. When this occurs, some of the liquid tends to remain trapped within the particles, and the particles themselves tend to pack together. In particular, if the particles are soft rather than rigid they tend to pack together to form a substantially impervious bed.

After as much as possible of the first liquid has been withdrawn, a second liquid is introduced into the vessel and the vessel is shaken again to allow the second liquid to come into contact with the support material. After a further predetermined period of time has elapsed the tap is re-opened and the second liquid is drained off in the same way that the first liquid was drained off. The process is then repeated with as many liquids as are required to complete the desired reaction or reactions.

As it is impossible to withdraw any of the liquids fully from the support material, each newly introduced liquid tends to be slightly contaminated with the previous liquid. This may lead to a reduced yield or to the need for the addition of extra steps in each of which the remaining unwanted liquid is washed by the introduction of a suitable liquid. An aim of the present invention is to enable those problems to be overcome or at least reduced.

From one aspect the present invention consists in a method of carrying out an organic chemical reaction in which a substance which takes part in the reaction is attached to particles of previous support material so that at least some of the substance is within the particles, a plurality of liquids is successively introduced into a vessel containing a quantity of that support material so that the material becomes immersed in each of those liquids successively and the reaction occurs as a consequence of the immersion of the quantity of support material in that succession of liquids, the introduction of at least one of the liquids into the vessel being carried out in such a manner that the immediately preceding liquid is progressively displaced by the incoming liquid, these two liquids being of different densities and the arrangement being such that, during the introduction of the incoming liquid into the vessel, the more dense of said two liquids is situated below the less dense of said two liquids.

An important feature of the present invention is the progressive displacement of one liquid by the next. As this occurs there is normally a reasonably well-defined boundary or interface between the two liquids. This progressive displacement is also referred to herein as layered displacement. An advantage of this progressive or layered displacement is that the incoming liquid tends to wash the previous liquid from inside the particles, so that the tendency for the one liquid to be contaminated by the preceding liquid is reduced.

When the incoming liquid is more dense than the liquid that immediately precedes it in the vessel, the incoming liquid is preferably introduced into the vessel from below. This helps to maintain the integrity of the two liquids and to prevent their mixing together For the same reason, when the incoming liquid is less dense than the liquid that immediately precedes it in the vessel, the incoming liquid is preferably introduced into the vessel from above.

The support material is normally such that when a particle of the material has been immersed in a liquid for a while and reaches an equilibrium with the liquid much of the overall volume of the particle is occupied by the liquid. Consequently, the density of the liquid-filled particle is substantially equal to the density of the liquid itself.

When particles of the support material are immersed in one liquid which is then progressively displaced by another liquid of a different density, as described above, the particles tend to remain in the one liquid and to move with that liquid, ahead of the incoming liquid. In a preferred method of carrying out the invention said one liquid, as it is displaced, passes through porous restraining means of a pore-size such that the support material cannot pass through it. As the incoming liquid progressively displaces the immediately preceding liquid the particles of support material tend to move towards the restraining means. Eventually the leading particles are restrained from further movement by the presence of the restraining means, the following particles pack against them, and this continues until a bed of packed particles of support material is formed against the restraining means. The incoming liquid then passes progressively through the bed and tends to displace the immediately preceding liquid from inside the particles of support material. This is found to be a particularly efficient method of replacing one liquid with another inside the particles.

Provided that the densities of the two successive liquids are significantly different a stable, coherent bed of support material is formed If the difference in density is very small, however, the bed may be less stable and there may be some slight movement of the constituent particles in the bed. Such a bed is referred to herein as a semi-packed bed. A method in accordance with the invention is nevertheless found to operate satisfactorily with a semi-packed bed.

When the incoming liquid has displaced the immediately preceding liquid from the support material, the overall density of each particle becomes very close to that of the incoming liquid As a result the forces acting on the particles to maintain them in a packed state are reduced, and at least some of the particles may become free from the bed. This does not affect the method adversely, however, as the particles concerned are those in which the incoming liquid has replaced the immediately preceding liquid.

In order to ensure that the bed of support material is fully broken up, the incoming liquid is preferably recirculated before it in turn is replaced, the recirculation including flow through the restraining means in a reverse direction. The recirculation is preferably continuous or substantially so and may be such as to cause the particles of support material to separate from one another and to move randomly around in the liquid in the vessel. The support material is then in a state referred to herein as fluidised.

It is generally desirable to cause the support material to become fluidised on each occasion after it has been formed into a bed and incoming liquid has been progressively passed through it. Fluidisation enables the new liquid to come into intimate contact with each particle of the support material individually. Also, where soft-gel support material is used, fluidisation enables each particle to achieve equilibrium with the liquid and, without restraint, to swell or shrink to a size dependent on the nature of the liquid. When the particles are subsequently formed into a new bed, there is then no tendency for over-tight packing to occur or for cracks or fissures to form in the bed, both of which phenomena would be disadvantageous as they would militate against the steady flow of the incoming liquid through the particles in the bed.

The bed or beds of particulate support material referred to above may be formed at or near the bottom of the vessel or at or near the top of the vessel, depending on the relative densities of the particles of support material and of the liquid in which they are immersed. It may therefore happen that a bed of particulate support material is immersed in a liquid of a relatively low specific gravity so that it resides at or near the bottom of the vessel and that as the next succeeding liquid is introduced into the vessel from below, being a liquid with a relatively high specific gravity, the bed rises as a whole to a position at or near the top of the vessel. Conversely a bed of support material supported at or near the top of the vessel in a relatively dense liquid may move downwards as a whole when a less dense liquid is introduced into the vessel from above. In general, however, it is preferred to break up the bed by recirculation before a new bed is formed.

It will be appreciated from the foregoing that during the progressive displacement of one liquid by another the direction of flow may be upwards or downwards, depending on the relative densities of the liquids. Apparatus for use in carrying out the invention may therefore employ upper and lower restraining means so that beds of support material can be formed against one or the other, depending on the direction of flow of the incoming liquid There are preferably two such restraining means spaced apart, one above the other, and defining between them an enclosure in which the support material is trapped. The restraining means or each restraining means preferably comprises a plate of a sintered material. Preferably the incoming liquid is introduced through one of the restraining means while the immediately preceding liquid escapes through the other restraining means. The incoming liquid preferably flows in through the whole or substantially the whole of the restraining means; this encourages uniform displacement of the immediately preceding liquid. Nevertheless it has been observed that even if part of the surface of a restraining means is blocked, the incoming liquid, after passing through the unblocked part of the restraining means normally spreads out over the whole of the surface of the restraining means, provided that the incoming liquid is introduced at a sufficiently slow rate.

While the invention includes within its scope a method in which the support material is immersed successively in only two liquids, it is envisaged that the invention will usually be employed in carrying out methods in which the support material is immersed in each in turn of a considerably greater number of liquids. Nevertheless it is also to be understood that one or more of the liquids may be introduced in a manner different from the manner that is characteristic of the present invention and in which the immediately preceding liquid is progressively displaced by the incoming liquid For example, it may be necessary or desirable for the support material at some stage to be immersed in one liquid and for it next to be immersed in a mixture of that liquid with another liquid. To achieve this result, some of that other liquid may be introduced into the vessel in such a manner as to mix with the immediately preceding liquid rather than to displace it completely.

While the invention can be used with support material comprising particles of any suitable form, including rigid particles such as those made from polystyrene, it is particularly suitable for use with a support material comprising a soft gel in particulate form. The use of such gels in carrying out organic chemical reactions is already well-known and well-understood, so the gels will not be further described here. As is already known, when such gels in particulate form are immersed in a liquid they absorb some of the liquid and swell to a size dependant on the nature of the liquid. When immersed in a succession of different liquids, the particles tend to change in size. When using a method in accordance with the present invention, in which the particles remain immersed, the particles can readily be caused to disperse temporarily and move relative to one another in order to accommodate the changes in size before being reformed into a new bed.

From another aspect the present invention consists in apparatus for use in carrying out a method according to the first aspect of the present invention and comprising a vessel for containing a quantity of support material in particulate form, the vessel having upper and lower permeable restraining means through which liquids can be introduced into and withdrawn from the vessel, and pumping means operative to pump liquid into the vessel from above and also operative to pump liquid into the vessel from below.

The apparatus preferably incorporates valve means which in one state enables liquid to be pumped into the vessel from above and in another state enables liquid to be pumped into the vessel from below. The valve means is preferably such that in said one state it guides liquid displaced from below to enter a return duct, and in said other state it guides liquid displaced from above to enter the return duct. There may also be subsidiary valve means which in one state connects the return duct to the inlet of the pump, and in another state connects a liquid supply tank to the inlet of the pump and connects the return duct to a discharge duct.

An embodiment of the present invention will now be described, by way of example only, with reference to the accompanying drawings, in which.

Figure 1:
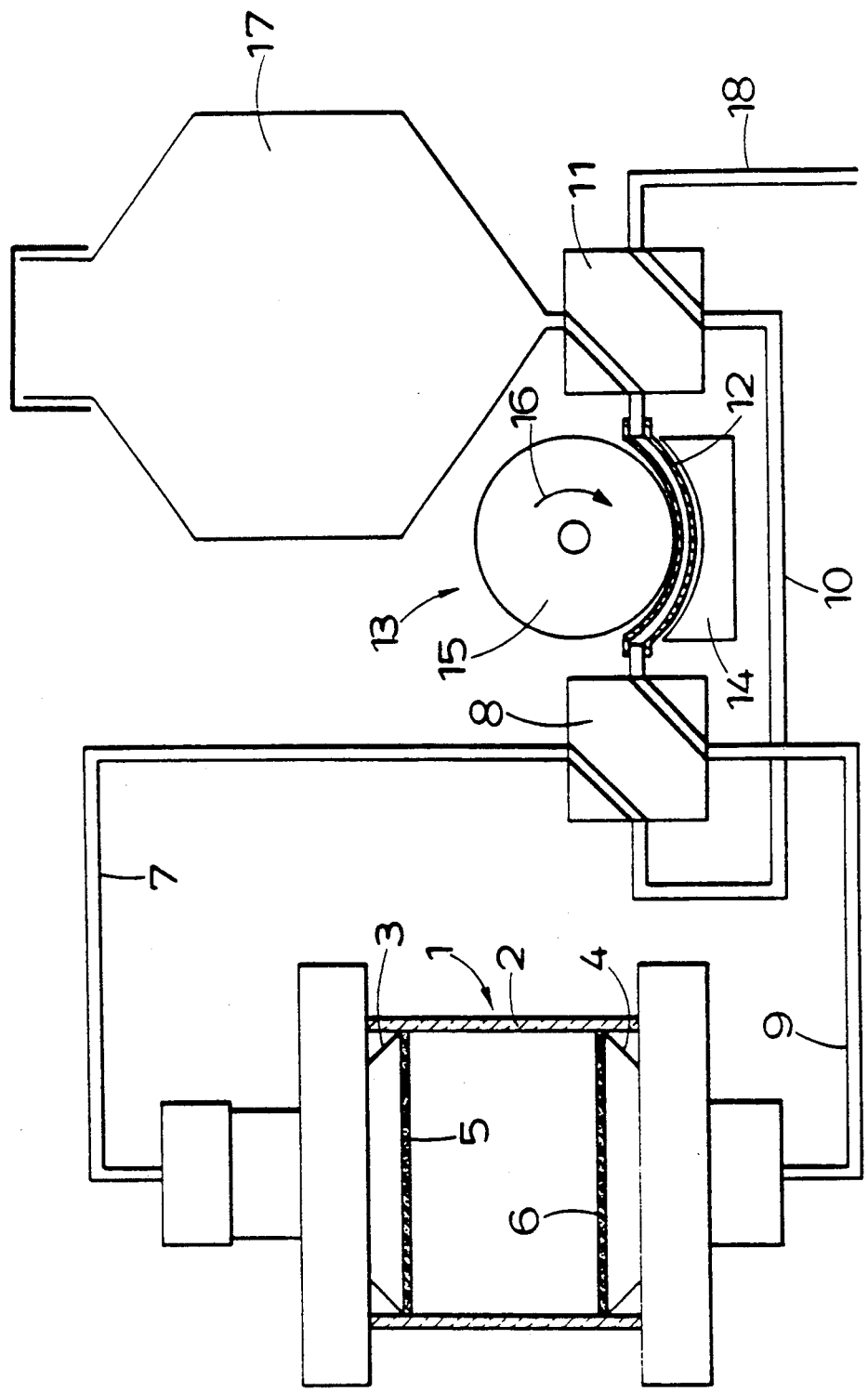
FIG. 1 is a diagrammatic view of apparatus embodying the present invention.

The apparatus illustrated is largely assembled from conventional components. The details of those components have no real bearing on the present invention and therefore the apparatus is shown in largely diagrammatic form.

The apparatus comprises a vessel 1 having a cylindrical wall 2, with its axis vertical, and frusto-conical end pieces 3 and 4 at the top and bottom respectively The lower end piece 4 is fixed relative to the wall 2 but the upper end piece 3 can be adjusted vertically so as to vary the internal volume of the vessel. A restraining plate 5 is mounted across the mouth of the upper end piece 3 and a similar plate 6 is mounted across the mouth of the lower end piece 4. The plates 5 and 6 are horizontal and each is made from sintered PTFE.

The upper end of the upper end piece 3 is connected by a tube 7 to a first port of a valve 8 which is a two-way, two-position rotary valve. The lower end of the lower end piece 4 is connected by a tube 9 to a second port of the valve 8, the first and second ports being opposed to each other so that in no position of the valve are they interconnected. A third port of the valve 8 is connected by means of a tube 10 to a first port of a valve 11 which is similar in construction and operation to the valve 8. The fourth port of the valve 8 is connected to one end of a length of flexible tubing 12 constituting part of a peristaltic pump 13. The tubing 12 is of arcuate form, being mounted between an arcuate abutment 14 and a rotor 15 which is provided with rollers (not shown) which engage the length of tubing 12 in the usual manner. The rotor is connected to a reversible motor (not shown) which is of variable speed and causes the rotor to rotate in the direction of the arrow 16. The other end of the length of tubing 12 is connected to a second port of the valve 11. A third port of the valve 11 is connected to the outlet of a reservoir 17, while the fourth port of the valve 11 is connected to a discharge tube 18.

The other end of the length of tubing 12 is made of a chemically inert material, a suitable material being that marketed under the trade mark Marprene. The other tubes 7, 9, 10 and 18 are also made from a chemically inert material, a suitable material being PTFE.

In use, a quantity of pervious support material (not shown) in particulate form is disposed in the vessel 1 between the upper and lower restraining plates 5 and 6. Preferably the material occupies more than half of the available volume, the material typically occupying about two thirds of that volume.

In a typical operation of the apparatus a first liquid is introduced into the reservoir 17. The valve 11 is turned to a first position (position I), in which the outlet of the reservoir is connected to the inlet of the pump 13, and the valve 8 is also turned to a first position (position I), in which the outlet of the pump 13 is connected to the tube 9. Both valves are illustrated as being in position I. The pump is operated to pump the first liquid from the reservoir 17 to the lower end piece 4 of the vessel 1. Excess liquid passes from the top of the vessel through the tube 7 to the valve 8 and thence through the tube 10 to the valve 11 and the discharge tube 18. When this occurs the valve 11 is turned to a second position (position II) such that the tube 10 is connected to the inlet of the pump 13 while the reservoir 17 is connected to the discharge tube 18. Continued operation of the pump causes the liquid to be recirculated through the vessel, while any remaining contents of the reservoir 17 are drained away through the discharge tube 18. The rate of operation of the pump is such that the particles of support material are in a fluidised state.

A second liquid is introduced into the reservoir and the valve 11 is returned to position I so that the second liquid is drawn through the pump 13. If, for the sake of example, the second liquid is more dense than the first liquid, the valve 8 is allowed to remain in position I and the second liquid is progressively introduced into the vessel through the tube 9. The rate of operation of the pump is such that the incoming second liquid progressively displaces the first liquid, the boundary between the two liquids moving steadily upwards. The particulate support material forms a bed against the upper restraining plate 5 as described above. When all of the first liquid has been discharged from the vessel 1 and the second liquid has reached the valve 11, the valve 11 is turned back to position II, while the valve 8 is turned to a second position (position II) in which the outlet of the pump 13 leads to the tube 7 while the tube 9 is connected to the tube 10. Consequently the second liquid is recirculated through the vessel in a direction the reverse of that in which it was first introduced into the vessel. This breaks up the bed and fluidises the support material which then circulates freely within the confines of the vessel between the restraining plates 5 and 6. It may well have happened that during their immersion in the second liquid the particles have changed in volume, for the extent to which each particle swells when immersed in a liquid often varies from liquid to liquid. If the particles had not been caused to circulate freely for a while in the second liquid, their change in volume would have tended to lead either to increased packing within the bed resulting in an increased resistance to flow of any subsequent liquid or to the formation of cracks or fissures through the bed resulting in a tendency for any subsequent liquid to flow through the cracks or fissures without permeating through the bed as is desired.

A plurality of other liquids can then be introduced, one after another, in much the same manner. When the incoming liquid is less dense than the preceding liquid it can be introduced into the vessel 1 from above by way of the tube 7, the valve 8 having been rotated to position II.

By suitable variation in the speed of the pump 13 and manipulation of the valves 8 and 11 various other effects may be obtained, as indicated above. For example, by turning valve 11 from position I to position II before one liquid has been only partially replaced by a subsequent liquid, and if necessary by increasing the speed of the pump, a mixture of liquids can be formed which is recirculated through the vessel 1.

When a reaction has been completed the support material, bearing the product of the reaction, may be withdrawn from the vessel and separated from it by known techniques.

It will be appreciated from the foregoing description of the apparatus illustrated that numerous variations in technique are possible In carrying out any particular chemical reaction, the sequence of techniques employed is preferably chosen so as to maximise the yield and minimise the contamination of the product with unwanted materials.

There follows an example of a reaction carried out by a method in accordance with the present invention and using apparatus of the kind illustrated.

EXAMPLE

This reaction consists of the synthesis of a calcitonin gene related peptide segment, CGRP (31-36).

The method employs an acid-catalyzed N-terminal deprotection strategy with t-butoxycarbonyl (Boc) amino groups.

Particulate support material was prepared. This comprises particles of crosslinked poly[N-[2-(4-hydroxyphenyl)ethyl]acrylamide] (Copolymer Q).

Copolymer Q, a de-O-acetylated bead form copolymer of N-[2-(4-hydroxyphenyl)ethyl]acrylamide and N,N'-diacryloylpiperidine (molar ratio 20/1), swollen volume in $HCONMe_2$ 10–20 $cm^3$ $g^{-1}$ copolymer, was prepared according to the literature (Epton, R. and Williams, A. *Int. J.Biol. Macromol.* 1981, 3, 336).

A solution of Boc-Ala-OH (2.37 g, 12.5 mmol) diisopropylcarbodiimide (DIC) (1.90 g, 15 mmol) in $HCONMe_2$ (15 $cm^3$) was added to Copolymer Q (0.5 g, phenol content 5.0 mmol $g^{-1}$) 4-dimethylaminopyridine (DMAP) (0.61 g, 5 mmol) was added with just sufficient $HCONMe_2$ (~15 $cm^3$) to permit nitrogen stirring. The reaction was allowed to proceed over 18 h at 25° C. with gentle nitrogen stirring Reagent solution was drained off and the gel beads washed repeatedly with $HCONMe_2$, $CH_2Cl_2$ and $Et_2O$ and dried to give Boc-Ala-O-[Copolymer Q] (0.93 g 2.3 mmol amino acid).

Boc-Lys(ClZ)-OH (1.24 g, 3 mmol) and 1-hydroxybenzotriazole (HOBt) (0.81 g, 6 mmol) in $HCONMe_2$ (7.5 $cm^3$) was chilled to 0° C. and diisopropylcarbodiimide (DIC) (0.34 g, 2.7 mmol) added. The solution was stirred gently and then allowed to warm to room temperature over 30 min. N-methylmorpholine (NMM) (0.20 g, 2 mmol) was added immediately prior to use.

Boc-Ser(Bzl)-OBt/HOBt solution was prepared in similar manner to Boc-Lys(ClZ)-OBt/HOBt solution (described in the preceding paragraph) from Boc-Ser(Bzl)-OH (0.88 g, 3 mmol).

Boc-Gly-OBt/HOBt solution was prepared in similar manner to Boc-Lys(ClZ)-OBt/HOBt solution from Boc-Gly-OH (0.43 g, 3 mmol).

Boc-Val-OBt/HOBt solution was prepared in similar manner to Boc-Lys(ClZ)-OBt/HOBt solution from Boc-Val-OH (0.65 g, 3 mmol).

Boc-Asn-OBt/HOBt solution was prepared in similar manner to Boc-Lys(ClZ)-OBt/HOBt solution from Boc-Asn-OH (0.70 g, 3 mmol).

-The vessel of the apparatus, which had a height of 2.5 cm and a diameter of 2.5 cm, was batched with Boc-Ala-O-[Copolymer Q] (0.37 g, 1 mmol amino acid). $3\text{-MeC}_6\text{H}_4\text{OH}/Cl_3\text{CMe}$ (4/1) was pumped in to fill the reactor by upward flow, and swelling was allowed to proceed with upward recycling over 1 h. The particles of copolymer moved freely in the vessel, this being referred to in the accompanying Table as a fluidised state of the bed. The appropriate standard CF peptide chain elongation cycles were then performed (see the Table). Each in turn of the five amino acid 1-benzotriazole ester/HOBt solutions described above was employed in a cycle of operations with the result that each in turn of the amino acid was added to the chain. Each cycle consisted of a prewash (or post-coupling wash), $CF_3CO_2H/3\text{-MeC}_6\text{H}_4\text{OH}/Cl_3\text{CMe}$ (5/4/1) mediated deprotection, post-deprotection washing, neutralisation by N-methylmorpholine (NMM) in $CHONMe_2$, post-neutralisation washing, treatment with an appropriate Boc amino acid 1-benzotriazole ester/HOBt/NMM solution to effect peptide chain elongation and, finally, post-coupling washing. Full operational and experimental details of the standard CF peptide chain extension cycles, together with details of reaction and washing solvents, are given in the Table. A non-standard CF peptide chain extension cycle, in which post-deprotection neutralisation and post-neutralisation washings were omitted (Table: Stages 4 and 5) in favour of relying solely on in situ neutralisation during the later peptide bond formation step, is described in Note 1 to the Table. This non-standard cycle was used to extend the peptide chain from Boc-Lys(ClZ)-Ala-O-[Copolymer Q] to Boc-Ser(Bzl)-Lys(ClZ)-Ala-O-[Copolymer Q].

Upon completion of the synthesis, the solvent-swollen gel assembly was removed from the reactor and washed repeatedly with $HCONMe_2$, $CH_2Cl_2$ and $Et_2O$ and then dried to give Boc-Asn-Val-Gly-Ser(Bzl)-Lys(ClZ)-Ala-O-[Copolymer Q] (Peptide-resin Assembly 1) (1.12 g).

Figure 2:
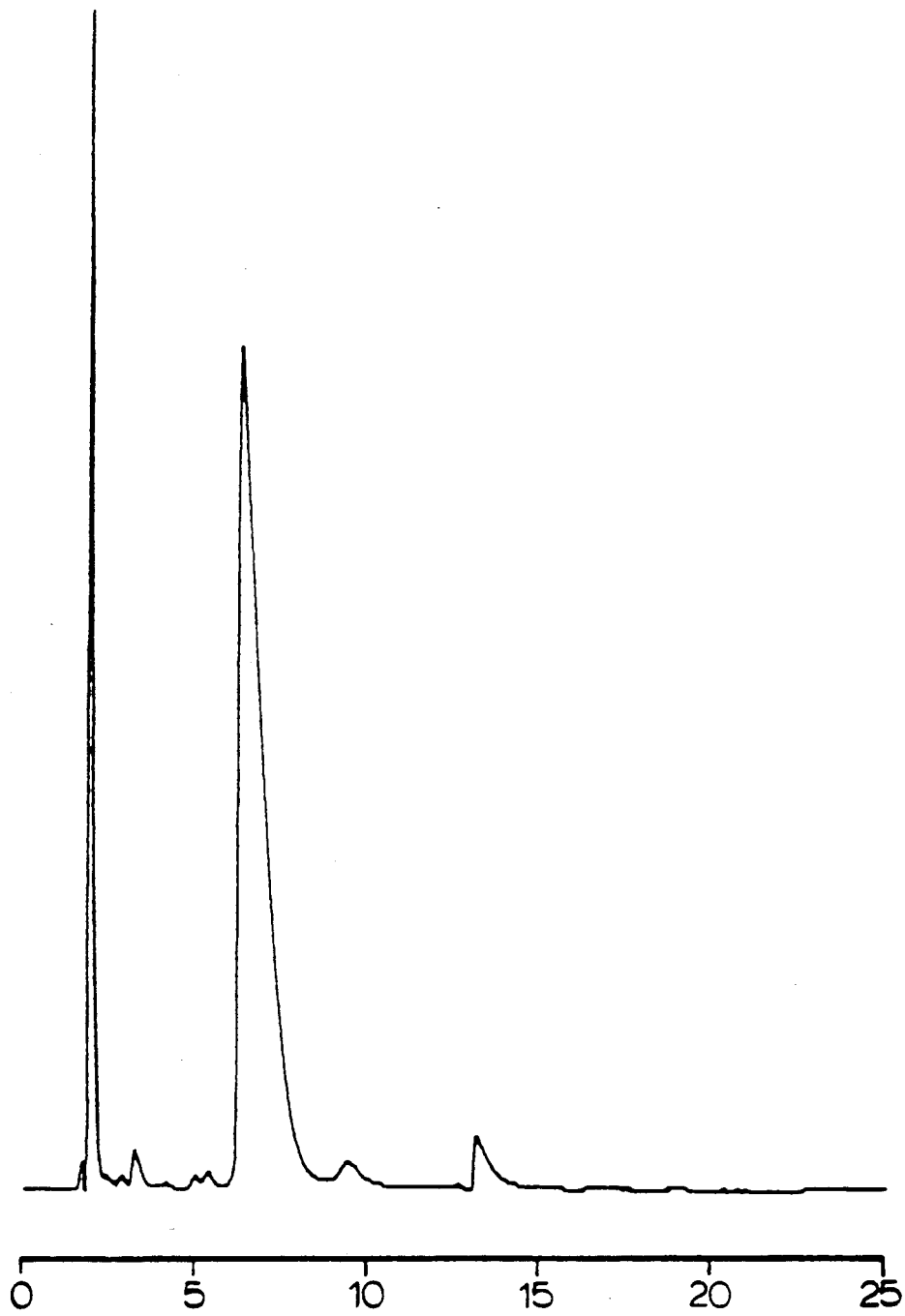
FIG. 2 is a graph of a chromatogram.

Peptide-resin Assembly 1 (50 mg) was allowed to swell to equilibrium in $HCONMe_2$ (1.98 $cm^3$) and 98% $NH_2NH_2.H_2O$ (0.02 $cm^3$) added with nitrogen stirring. Reaction was allowed to proceed for 2 min, after which the reaction liquor was drawn into $Et_2O$ (50 $cm^3$), pre-chilled at −78° C., and the precipitate collected and dried to give Boc-Asn-Val-Gly-Ser(Bzl)-Lys(ClZ)-Ala-NHNH$_2$ (~39 mg). An HPLC chromatogram for this compound, performed on a Waters Novapak reversed phase C-18 radial pak cartridge (100×8 mm) with 42% aqueous MeCN as eluent at a flow rate of 1.5 $cm^3$ $min^{-1}$, is shown in FIG. 2. IN this graph the horizontal axis represents time and is calibrated in minutes.

The foregoing example illustrates the use of the invention in peptide synthesis by a method employing an acid-catalyzed N-terminal deprotection strategy with Boc amino acids. The invention can equally well be used in peptide synthesis by a method employing an aminolytic N-terminal deprotection strategy with fluorenylmethoxycarbonyl amino acids.

TABLE

Details of operations involved in performing a standard 1 mmol scale ultra-high load CF chain extension cycle with acid-catalysed N-terminal deprotection (Boc amino acids).

| Stage of cycle | Reagent or solvent | Flow Direction in Vessel |
|---|---|---|
| 1. prewash | 1a. 3-MeC$_6$H$_4$OH/Cl$_3$CMe(4/1) | up |
| 2. Deprotection | 2a. CF$_3$CO$_2$H | up |
| | 2b. CF$_3$CO$_2$H (5 min) | down |
| | 2c. CF$_3$CO$_2$H/3-MeC$_6$H$_4$OH/Cl$_3$CMe (5/4/1) (25 min) | up |
| 3. Post-deprotection wash | 3a. 3-MeC$_6$H$_4$OH/Cl$_3$CMe (4/1) | down |
| | 3b. 3-MeC$_6$H$_4$OH/Cl$_3$CMe (4/1) | up |
| | 3c. HCONMe$_2$ | down |
| | 3d. HCONMe$_2$ | up |
| 4. Neutralisation (Note 1) | 4a. NMM | down |
| | 4b. NMM/HCONMe$_2$ (1/9) | up |
| 5. Post-neutralisation wash (Note 1) | 5a. HCONMe$_2$ | up |
| | 5b. HCONMe$_2$ | down |
| 6. Coupling | 6a. Boc—AA—OBt/HoBt/NMM HCONMe$_2$ | up |
| | 6b. Boc—AA—OBt/HoBt/NMM HCONMe$_2$ (60 min) (Note 2) | up |
| 7. Post-coupling wash | 7a. HCONMe$_2$ | down |
| | 7b. HCONMe$_2$ | up |
| | 7c. 3-MeC$_6$H$_4$OH/Cl$_3$CMe (4/1) | up |
| | 7d. 3-MeC$_6$H$_4$OH/Cl$_3$CMe (4/1) | down |

| Stage | Operation | Delivery mode |
|---|---|---|
| 1a. | Washing | Uniform |
| 2a. | Dispensing | Uniform (layered displacement) |
| 2b. | Back cycle/deprotection | Mixing |
| 2c. | Deprotection | Uniform circulation |
| 3a. | Washing | Uniform (layered displacement) |
| 3b. | Washing | Uniform |
| 3c. | Washing | Uniform (layered displacement) |
| 3d. | Washing | Uniform |
| 4a. | Dispensing | Uniform (layered displacement) |
| 4b. | Back cycle/neutralisation | Mixing/Uniform circulation |
| 5a. | Washing | Uniform (layered displacement) |
| 5b. | Washing | Uniform |
| 6a. | Dispensing | Uniform (layered displacement) |
| 6b. | Recycle to couple | Uniform |
| 7a. | Washing | Uniform (layered displacement) |
| 7b. | Washing | Uniform |
| 7c. | Washing | Uniform (layered displacement) |
| 7d. | Washing | Uniform |

| Stage | State of bed of support material | Reagent or solvent used or added | Position of value 8 | Position of value 11 |
|---|---|---|---|---|
| 1a. | Fluidised | 30 cm$^3$ | I | I |
| 2a. | Packed at top | 10 cm$^3$ | I | I |
| 2b. | Fluidised | none | II | II |
| 2c. | Fluidised | none | I | II |
| 3a. | Packed at bottom | 30 cm$^3$ | II | I |
| 3b. | Fluidised | 30 cm$^3$ | I | I |
| 3c. | Packed at bottom | 30 cm$^3$ | II | I |
| 3d. | Fluidised | 30 cm$^3$ | I | I |
| 4a. | Semi-packed | 2.0 cm$^3$ | II | I |

TABLE-continued

Details of operations involved in performing a standard 1 mmol scale ultra-high load CF chain extension cycle with acid-catalysed N-terminal deprotection (Boc amino acids).

| | | | | |
|---|---|---|---|---|
| | towards bottom | | | |
| 4b. | Fluidised | none | I | II |
| 5a. | Fluidised | 30 cm³ | I | I |
| 5b. | Packed at bottom | 30 cm³ | II | I |
| 6a. | Semi-packed towards top | 7.5. cm³ | I | I |
| 6b. | Fluidised | none | I | II |
| 7a. | Packed | 30 cm³ | II | I |
| 7b. | Fluidised | 30 cm³ | I | I |
| 7c. | Packed | 30 cm³ | I | I |
| 7d. | Packed | 30 cm³ | II | I |

Note 1. On progressing peptide chain elongation from the dipeptide to tripeptide stage, a non-standard chain elongation cycle was performed in which post-deprotection neutralisation and post-neutralisation washings were omitted (Stages 4 and 5). This was necessary to prevent the free aminoterminal of the dipeptide attacking the phenyl ester anchoring linkage and causing deloading via diketopiperazine formation Note 2. For Boc—Gly—OBt coupling time was 90 min.

We claim:

1. A method of carrying out an organic chemical reaction in which a substance which takes part in the reaction is attached to particles of pervious support material so that at least some of the substance is within the particles, a plurality of liquids is successively introduced into a vessel containing a quantity of that support material so that the material becomes immersed in each of those liquids successively and the reaction occurs as a consequence of the immersion of the quantity of support material in that succession of liquids, the method being characterised in that the introduction of at least one of the liquids into the vessel is carried out in such a manner that the immediately preceding liquid is progressively displaced by the incoming liquid, these two liquids being of different densities and the arrangement being such that, during the introduction of the incoming liquid into the vessel, the more dense of said two liquids is situated below the less dense of said two liquids.

2. A method according to claim 1 characterised in that the pervious support material comprises a soft gel in particulate form.

3. A method according to claim 1 characterised in that said incoming liquid is more dense than said immediately preceding liquid and is introduced into the vessel from below.

4. A method according to claim 1 characterised in that said incoming liquid is less dense than said immediately preceding liquid and is introduced into the vessel from above.

5. A method according to claim 3 characterised in that said immediately preceding liquid, as it is displaced, passes through porous restraining means of a pore-size such that the support material cannot pass through it.

6. A method according to claim 2 characterised in that at least one of said liquids is recirculated after its initial introduction into the vessel, the direction of flow being the reverse of that in which the liquid was initially introduced into the vessel.

7. A method according to claim 2 characterised in that said incoming liquid is introduced into the vessel through a porous restraining means having pores of too small a size to allow the particles of support material to pass through them.

8. Apparatus for use in carrying out a method according to claim 1 characterised in that it comprises a vessel for containing a quantity of support material in particulate form, the vessel having upper and lower permeable restraining means through which liquids can be introduced into and withdrawn from the vessel, a pumping means operative to pump liquid into the vessel from above and also operative to pump liquid into the vessel from below, and a first valve means, wherein said valve means has a first and second state and in one of said states connects a return duct to an inlet of said pump and in the second of said states connects a liquid supply tank to said inlet of said pump and connects the return duct to a discharge duct.

9. Apparatus according to claim 8 characterised in that it incorporates a second valve means (8) which in one state enables liquid to be pumped into the vessel from above and in another state enables liquid to be pumped into the vessel from below.

10. Apparatus according to claim 9 characterised in that the valve means (8) is such that in said one state it guides liquid displaced from below to enter a return duct (10), and in said other state it guides liquid displaced from above to enter the return duct.

11. Apparatus according to claim 8 characterised in that the pump is a peristaltic pump.

* * * * *